United States Patent
Olcina Portilla

(10) Patent No.: US 10,945,833 B2
(45) Date of Patent: Mar. 16, 2021

(54) ACCOMMODATIVE INTRAOCULAR LENS

(71) Applicant: LENS UNDERGONE ZONULA GLOBAL, S.L., Valencia (ES)

(72) Inventor: Luis Ignacio Olcina Portilla, Valencia (ES)

(73) Assignee: LENS UNDERGONE ZONULA GLOBAL, S.L., Valencia (ES)

(*) Notice: Subject to any disclaimer, the term of this patent is extended or adjusted under 35 U.S.C. 154(b) by 49 days.

(21) Appl. No.: 15/776,717

(22) PCT Filed: Nov. 15, 2016

(86) PCT No.: PCT/ES2016/070813
§ 371 (c)(1),
(2) Date: May 16, 2018

(87) PCT Pub. No.: WO2017/085344
PCT Pub. Date: May 26, 2017

(65) Prior Publication Data
US 2018/0296323 A1 Oct. 18, 2018

(30) Foreign Application Priority Data
Nov. 16, 2015 (ES) .................................. 201531654

(51) Int. Cl.
*A61F 2/16* (2006.01)

(52) U.S. Cl.
CPC .... *A61F 2/1635* (2013.01); *A61F 2002/1682* (2015.04); *A61F 2002/1689* (2013.01); *A61F 2002/16901* (2015.04)

(58) Field of Classification Search
CPC .................. A61F 2/1635; A61F 2/1648; A61F 2002/1682; A61F 2002/1689; A61F 2002/16901
See application file for complete search history.

(56) References Cited

U.S. PATENT DOCUMENTS

| | | | |
|---|---|---|---|
| 2003/0158560 A1* | 8/2003 | Portney | A61F 2/1664 606/107 |
| 2007/0156236 A1* | 7/2007 | Stenger | A61F 2/1635 623/6.13 |
| 2011/0295368 A1 | 12/2011 | Bester | |
| 2013/0190868 A1* | 7/2013 | Kahook | A61F 2/1648 623/6.41 |
| 2014/0121768 A1 | 5/2014 | Simpson | |
| 2014/0172092 A1 | 6/2014 | Carson et al. | |
| 2014/0180404 A1 | 6/2014 | Tran | |
| 2014/0180406 A1 | 6/2014 | Simpson | |

* cited by examiner

*Primary Examiner* — Leslie Lopez
(74) *Attorney, Agent, or Firm* — Vedder Price P.C.

(57) ABSTRACT

IOL of the type which include a lens, haptics and a curving ring wherein there are soft haptics and rigid haptics, both being associated through a lever and wherein a softer outer ring houses in its inner geometry an inner curving ring, the latter being rigid and incomplete, with curving flaps in whose geometry the assembly consisting of lens and haptics is housed.

13 Claims, 5 Drawing Sheets

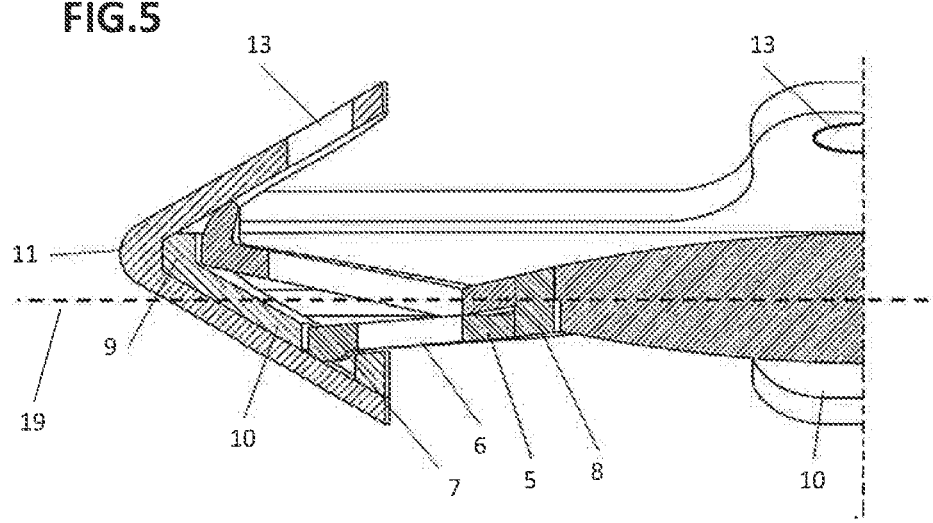

ACCOMMODATIVE INTRAOCULAR LENS

CROSS-REFERENCE TO RELATED APPLICATIONS

This application is a national stage application that claims the benefit of and priority from International Application No. PCT/ES2016/070813, filed May 26, 2017, which claims the benefit of and priority from Spanish Application No. P201531654, filed Nov. 16, 2015, both of which are wholly incorporated herein by reference.

The present invention relates to a new model of accommodative intraocular lens (IOL) which allows varying its focus due to the displacement of the lens and changes in thickness by curving.

The technical field which the present invention relates to is that of intraocular implants, and more specifically the field of lenses that are implanted inside the capsular bag after crystalline lens extraction.

BACKGROUND

The replacement of natural lenses with implants has become a common intervention in the field of ophthalmic surgery.

One of the problems that arise following this surgery is the inability to see at near and far ranges when using a monofocal IOL, since it is fixed inside the capsular bag and only one focal point can be chosen, so external lenses are additionally needed.

In contrast, multifocal IOLs provide two or more focusing distances thus avoiding the use of external lenses, as they allow vision correction at all distances.

However, multifocal IOLs have drawbacks such as low visual acuity and the appearance of halos around light sources, among others.

These limitations have encouraged studying the possibility of implanting accommodating lenses, which are lenses with one focal point, but they act like a multifocal IOL in being designed with a joint similar to the mechanics of the crystalline lens and through the action of the eye muscles, so the single focal point can vary to focus on objects at varying distances.

Among the accommodation mechanisms, the eye has been found to undergo a series of modifications such as; pupil contraction, ciliary muscle contraction, relaxation of the zonular ligament and changes in the size of the crystalline lens, such as: an increase in its thickness and in the curvature of the anterior face thereof.

There are several theories to explain the physiological mechanism of accommodation, which include those by Helmholtz, Tscherning, Gullstrand and Pflugk, in which the action of the ciliary muscle on the eye, the crystalline lens and the curving of its anterior face are noteworthy aspects.

Importantly, the capsular bag has much elasticity, since when it ruptures it retracts such that the rupture expands, as well as the folds that appear when the capsular bag is empty, disappear completely when expanded.

After extraction of the crystalline lens, the posterior capsule slackens on opening the anterior capsule, thereby eliminating its effects within the eye, and the posterior capsule may even move further in the anterior sense as it is not retained by the anterior capsule.

This phenomenon is observed in crystalline lens surgery and sometimes the posterior capsule ruptures due to capsulorrhexis upon increase of the posterior vitreous pressure.

A lens that can replace the functions of the crystalline lens would bring us closer to real accommodation.

A desirable lens for accommodation is one that is deformed due to the response of a force applied to the equator of the lens.

Under the influence of this force, the lens bulges in the axial direction, causing the posterior and/or anterior faces to curve much more, and therefore generating an increase in the accommodation capacity of the lens, that is to say, the greater the capacity of a lens to deform, the greater its capacity for accommodation.

A number of implants have been designed that attempt to use the contraction and relaxation of the ciliary muscle to change the optical capacity of the eye.

In general, IOLs comprise an optical part that ensures the optical and especially refractive correction and a haptic part that allows the movement of the lens.

Patent US2002/0138140 A1 uses a ring device, being flexible and deformable when the ciliary muscle contracts, whose design is aimed to allow the movement of the lens haptics and exert the effect of the ciliary muscle, to favour accommodation, which is shown in the figures when describing a posterior distension of the posterior capsule.

However, the design of the IOL of patent US2002/0138140 A1 does not allow the use at any time of the capsular distention as a movement amplification mechanism, nor does is change either the curvature or the thickness of the lens.

U.S. Pat. No. 666,003B1 describes a lever system wherein some branches rotate on other branches increasing accommodation by converting the radial movement of the capsular bag into a movement of axial amplification of the lens, wherein the haptics or ring have been designed so as to be flexible and thus transmit the contraction of the ciliary muscle. However, its design does not allow movement of the haptics, so that maximum relaxation of the capsular bag cannot be achieved.

The closest reference is found in Spanish patent P201000246, also belonging to the applicant, which describes an accommodating IOL to be placed it in the capsular bag after extraction of the crystalline lens, which increases the accommodation ability comprising at least an optical part, a haptic part, a curving flap, an incomplete curving ring and means for the displacement of the haptic part.

This patent enhances the above-mentioned one by simplifying its manufacture, by adding elements for its easier placement and alignment within the capsular bag.

Therefore, there is a need to provide an IOL comprising means to permit movement of the lens as well as increased deformation of the anterior and/or posterior faces of the lens, resulting in a greater capacity of accommodation.

DESCRIPTION OF THE INVENTION

Therefore, the object of the present invention is a new accommodating IOL that amplifies the accommodation power of the lens.

The present invention provides an accommodating IOL to be placed in the capsular bag after extraction of the crystalline lens, which increases the capacity of accommodation, which comprises:

At least an optical part, a soft haptic part, a rigid haptic part, an incomplete rigid and deformable inner curving ring with at least one curving flap and a soft outer curving ring with angled flaps.

The terms "soft" and "rigid" must be understood in relationship with each other and thus, the haptic part, of the two, having a lower resistance to elastic deformation will be considered the "soft" part, and the haptic part having greater resistance to elastic deformation will be considered the "rigid" part; similarly the ring, preferably the outer ring, having a lower resistance to elastic deformation will be considered the "soft" ring, and the ring which of the two has a greater resistance to elastic deformation will be considered the "rigid" ring.

1.—At Least One Optical Part:

The optical part is made of a deformable flexible material and whose refractive index is similar to that of any lens for intraocular use and that may comprise on its peripheral edge one or more notches arranged parallel to the axis that passes through the centre of the lens.

When the peripheral edge of the lens comprises more than one notch, the notches may be arranged symmetrically or equidistant and parallel to the axis that passes through the centre of the lens.

The maximum number of notches is determined by that allowed by the perimeter of the lens.

Such notch or notches are optional.

2.—A Soft Haptic Part:

The soft haptic part comprises radial extensions, preferably four and preferably equidistant to each other, made of a soft material, preferably the same material as the lens.

The term radial is to be understood as that such extensions start in the periphery of the optical part and extend outward away from the optical part.

The term soft haptic refers to each of these extensions while the term soft haptic part refers to the set of all the soft haptics.

Each of these soft haptics comprises an insertion channel and a centering hole, the insertion channel being intended to accommodate the lever of the rigid haptics as later explained.

The number of soft haptics can be variable, with a minimum of two and up to the maximum number allowed by the perimeter of the lens.

3. One or More Rigid Haptics:

Made from a material having a greater resistance to elastic deformation than that of the soft haptics, the rigid haptics comprise a main body, essentially flat, which presents a thickening at one of its ends and a tab on the opposite side, preferably on the reverse side.

This tab has a suitable geometry to lodge in the insertion channels of the soft haptics and to function as the resistance arm of a lever forcing the displacement and deformation of the optical part.

The tab, to promote its lever effect, preferably presents a perpendicular position with respect to the longitudinal axis of the soft haptic. These tabs will be referred to as levers.

The body of these rigid haptics presents a centering hole. There will preferably be as many rigid haptics as soft haptics.

4.—An Incomplete Inner Curving Ring, Preferably Rigid:

This inner ring is incomplete such that, even when made preferably of more rigid material, it is susceptible to elastic deformation and makes certain deformation possible.

The inner ring presents a series of curving flaps with clipping slots, termed curving flaps, these slots being suitable for the insertion therein of the thickenings present at the ends of the rigid haptics.

5.—An Outer Ring, Preferably Soft:

The outer ring has a grooved body, open towards the inside, suitable to house the rigid curving ring inside.

The outer ring has a series of angled flaps referred to as angled flaps of the outer ring.

These angled flaps of the outer ring is present centering holes.

As indicated, in a preferred embodiment the outer ring is made of a material that presents a lower resistance to elastic deformation than in the case of the inner ring, although it could happen that the exterior outer ring has the same rigidity or the same elasticity as the inner ring.

The rigid ring and the soft ring are joined forming a single piece for their easier insertion into the capsular bag.

The various elements described are grouped together forming two distinct groups, thus facilitating surgery.

A first group of elements comprising:

1. Optical part
2. Soft haptic part that comprises the soft haptics with their insertion channel and centering hole of the soft haptics.
3. Rigid haptics with their centering hole of the rigid haptics, thickening and lever A second group of elements comprising:

4. Inner ring, preferably rigid, incomplete, with its curving flaps that have clipping holes.
5. Outer ring, preferably soft, with its grooved body open to the inside and the angled flaps with centering hole The optical part and the soft haptic part are integrally joined or made in single piece, both parts being made of flexible, deformable material, and at least the optical part having a similar refractive index to that of any lens for intraocular use.

The soft haptic part comprises a series of extensions, each of which are referred to as soft haptics as already explained.

The optical part occupies a central position from which the soft haptics extend outwards, preferably radially.

Each of these soft haptics presents an insertion channel, a centering hole and a protrusion on its reverse side, and is slightly angled with respect to the horizontal axis of the optical part.

The angulation of the soft haptics with respect to the horizontal axis of the optical part is between 5° up to 180°.

Associated with each of the soft haptics, a rigid haptic is provided which inserts its lever in the insertion channel of each of the soft haptics.

An embodiment would be possible wherein not all the soft haptics have an associated rigid haptic although the embodiment chosen, and on which the description is based, is that each soft haptic has associated a rigid haptic.

On the mounted lens, the centering holes of the soft haptics and those of the rigid haptics are coincident, i.e. are overlapping.

The group formed by optical part, soft haptics and rigid haptics is housed in the inner ring making the thickenings existing on the rigid haptics coincide with the clipping slots existing on the curving flaps.

The inner ring is housed by the internal geometry of the outer ring thanks to the grooved shape, open to the inside, of the body of the latter.

The proper position of the assembly formed by inner ring, optical part, soft haptics and rigid haptics with respect to the outer ring will exist when the centering holes of the soft haptics and the centering holes of the angled flaps of the outer ring overlap.

Several advantages result from this structure.

In addition to lens displacement caused by the required means such as the haptics, accommodation is increased by the curving and/or changes in the thickness of the lens and/or distension of the posterior capsule and anterior capsule.

If we consider that the most important changes that occur when removing the lens are that, after surgery, the central part of the anterior capsule has been eliminated and the tension of the capsules is lost when the bag is empty, a new model of lens is proposed which achieves the postero-anterior displacement of the lens, a modification of the curvature of the lens and changes in lens thickness helped by the maximum distention of the crystalline capsule, which being as elastic as possible can favour this movement.

The lens moves using the contraction of the ciliary muscle and by the elastic return of the capsule as well as by the displacement of the posterior capsule forward due to the vitreous pressure, achieving a greater accommodative capacity by adding to the displacement, a curving.

In this description, the terms "anterior" and "posterior" are to be understood by their meanings as used in ophthalmology, i.e. "anterior" means that the lens is closer to cornea and "posterior" means that the lens is farther away from the cornea; these adjectives have also been used for devices that comprise the lens.

To this end, the accommodating lens of the present invention is provided with haptics and an incomplete inner curving ring having sufficient rigidity to maintain the capsular bag open and tensed such that the elastic capacity of the bag remains intact for the most part.

The advantage of keeping the bag completely distended and open, is that the latter is more sensitive to the elastic movement and postero-anterior displacement of the posterior capsule upon contraction of the ciliary muscle and increase of the pressure of the vitreous cavity and its contents, facilitating both the movement of the lens and its return to its resting position without obstacles as the contraction of the ciliary muscle stops.

The incomplete inner curving ring, due to its rigidity, allows the lens to remain stable when not accommodating and causes changes in the curvature and thickness of the lens when accommodating, as it retains the curving flaps and allows movement towards the centre when the lens rises.

If the lens has notches in its perimeter, the lens curvature may be modified, thereby achieving a greater accommodative capacity.

Accommodation is also increased by combining several optical parts in the same lens.

The materials of which the various components of the accommodating IOL are made are biocompatible materials for intraocular use such as acrylates and methacrylates (for example, polymethyl methacrylate), silicone, elastomer, among others.

These materials are elastically deformable allowing the lens to fold for insertion in the capsular bag through a small incision, and at the same time they are sufficiently rigid to maintain the capsular bag fully open and tensed.

BRIEF DESCRIPTION OF THE FIGURES

FIG. 5 shows a sectional view of half of the lens.

Figure 1:
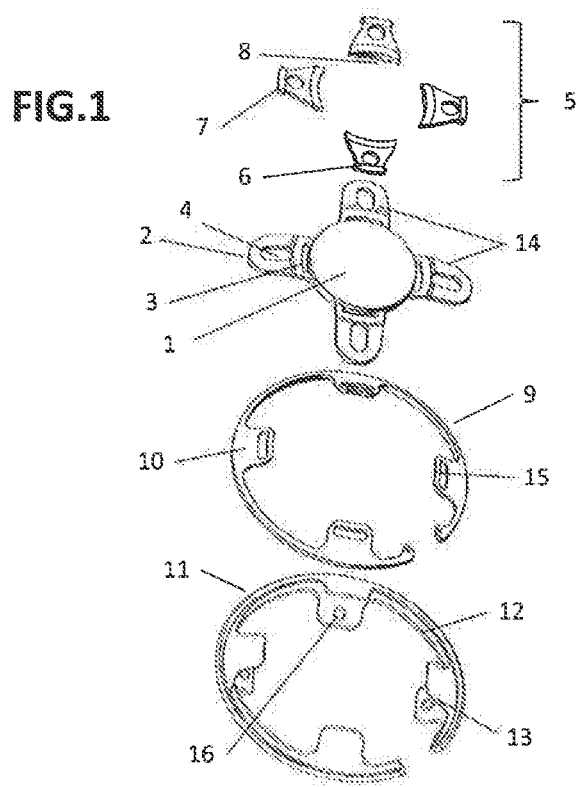
FIG. 1 is an exploded view of the various elements of the IOL and thus we find:
Optical part (1)
Soft haptic part (2) which comprises the soft haptics (14).
Insertion channel (3)
Centering hole of the soft haptics (4)
Protrusion (18)
Rigid haptics (5)
Centering hole of the rigid haptics (6)
Thickening (7)
Lever (8)
Incomplete inner ring (9)
Curving flaps (10) with clipping hole (15).
Outer ring (11)
Grooved body (12)
Angled flaps (13) with centering hole (16)
Figure 2:
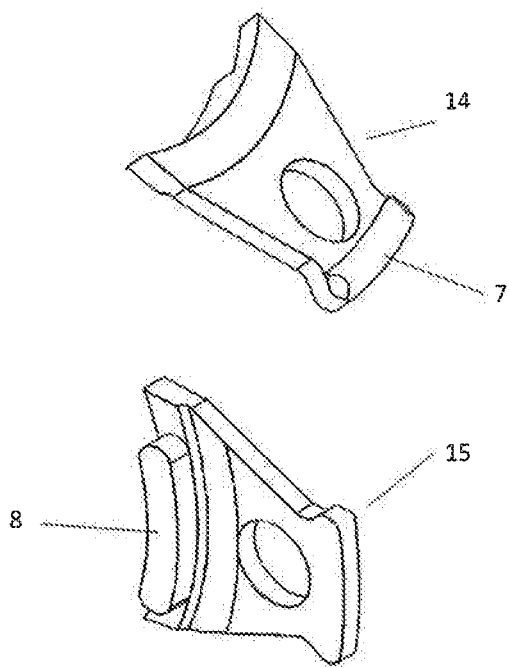
FIG. 2 shows in detail the front (14) and the reverse side (15) of the rigid haptic, the reverse side been taken as the side that will face the soft haptic, this figure showing the lever (8) and the thickening (7) cited in FIG. 1.
Figure 3:
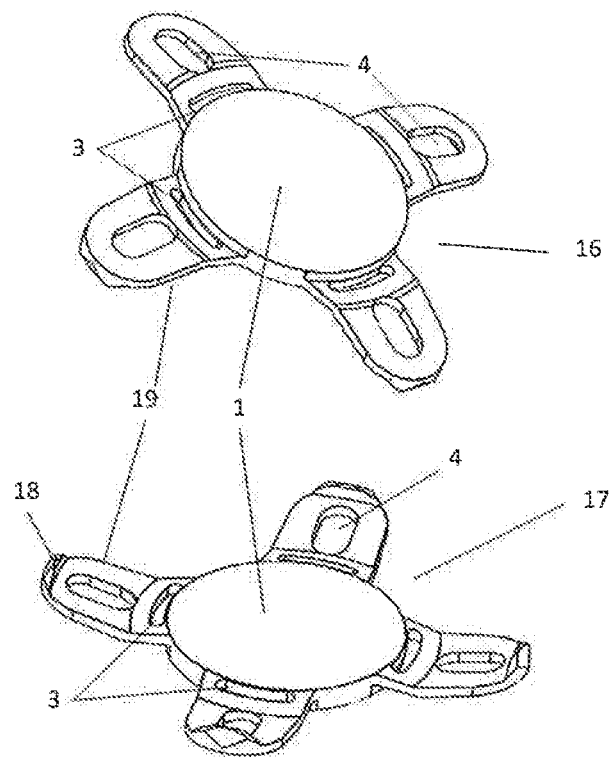
FIG. 3 shows the front of the lens and soft haptics (16) as well as the reverse side of the lens and soft haptic (17), highlighting protrusions (18) existing on the reverse side (17) at the end of the soft haptics (14), this figure also showing the optical part (1), the insertion channels (3) and the centering holes of the soft haptics (4).
Figure 4:
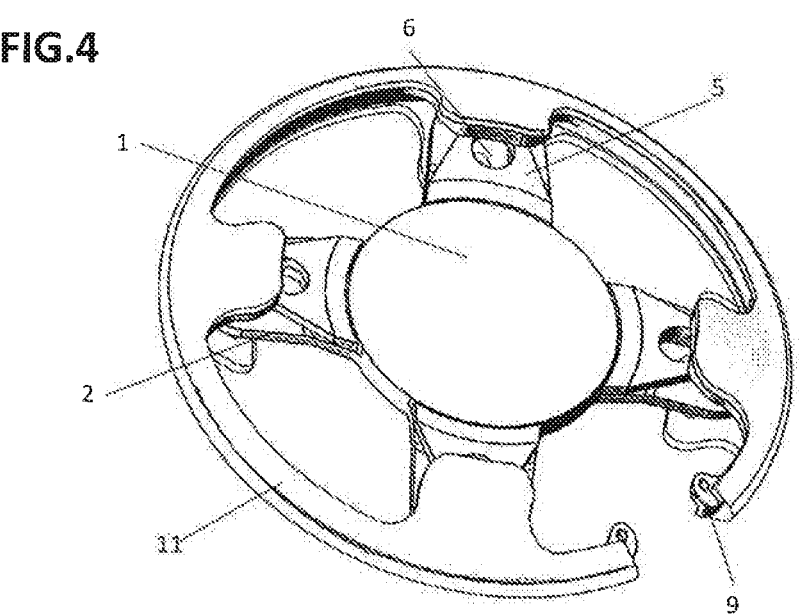
FIG. 4 shows the mounted lens and the outer ring (11) which houses the incomplete inner ring (9) sticking out, the rigid haptics (5) with their centering holes for the rigid haptics (6), the optical part (1) and the haptic part (2).

This figure shows the outer ring (11) with the angled flaps (13) with centering hole (16), the incomplete inner ring (9), the rigid haptics (5), their lever (8), the thickening (7) inserted in the clipping hole (15) of the curving flap (10) and the centering hole of the rigid haptics (6). Also shown is the horizontal axis (19) of the lens in respect of which the haptics present some degree of angulation.

DESCRIPTION OF AN EMBODIMENT OF THE INVENTION

An embodiment of the invention will now be described, this not being the only embodiment possible nor limiting the scope of the invention, but merely explanatory, while the invention encompasses any form of implementation that comprises the claimed technical solutions.

The invention relates to an accommodating IOL for its insertion into the capsular bag following the extraction of the crystalline lens that comprises:
Optical part (1)
Soft haptic part (2) which comprises the soft haptics (14).
Insertion channel (3)
Centering hole of the soft haptics (4)
Protrusion (18)
Rigid haptics (5)
Centering hole of the rigid haptics (6)
Thickening (7)
Lever (8)
Incomplete inner ring (9)
Curving flaps (10) with clipping hole (15).
Outer ring (11)
Grooved body (12)
Angled flaps (13) with centering hole (16)

The optical part (1) and the soft haptic part (2), comprising the soft haptics (14), are made in a single piece and of an elastically deformable material, the optical part having a similar refractive index to that of any lens of intraocular use.

The soft haptic part (2) comprises four soft haptics (14) extending radially from the perimeter of the optical part as extensions.

Each of these soft haptics comprises a insertion channel (3), a centering hole of the soft haptic (4) and a protrusion The protrusion (18) of the soft haptics (14) in lodging into the angled flaps (13) contributes to fix the assembly of lens and soft and rigid haptics to the outer ring (11) and serves as a stop to improve the curving of the lens when there is a postero-anterior displacement of the optical part of the lens.

Associated with these soft haptics (14) the rigid haptics (5) are provided, these being understood as a series of haptics whose resistance to elastic deformation is greater than that of the soft haptics.

Each one of these rigid haptics (5) comprises at the end of its reverse side a lever (8) having suitable geometry to be inserted in the insertion channel (3) of the soft haptics and thus the soft haptics become associated to the rigid haptics.

The rigid haptics (5) also comprise a thickening (7) at the end opposite to the lever (8), this thickening being suitable to be lodged in the clipping hole (15) of the curving flaps (10) of the inner ring (9).

Thus an assembly is configured that comprises an optical part (1), soft haptics (14), and rigid haptics (5).

The assembly described in the preceding paragraph is associated with another group or assembly comprising a rigid inner ring (9) with curving flaps (10), that is housed in the grooved body (12) of a soft outer ring (11).

The connection and attachment points between the assemblies are the thickenings (7) lodged into the clipping holes (15) and the protrusions (18) lodged in the angled flaps (13) of the outer ring.

This outer ring comprises a series of angled flaps (13) distributed in the same way as the curving flaps (10) of the inner ring (9).

These flaps are double arranged in pairs, a upper one and a lower one, wherein in each pair, at least one of them presents a centering hole.

In accordance with the foregoing, the accommodating lens is provided in two groups of independent elements, yet integral relative to each other.

On the one hand the assembly formed by the lens with its soft and rigid haptics, on the other the assembly consisting of the inner ring and the outer ring.

This provides a better implantation inside the capsular bag since the assembly consisting of the inner ring and outer ring, and then the assembly consisting of the optical part, soft haptics and rigid haptics are inserted separately, and through a simple mechanism of rotation the two assemblies are integrally joined to form a stable assembly but with a large displacement and curving capacity. Also the proper position can be checked by the positioning holes of the haptics and angled flaps.

The invention claimed is:

1. An accommodative intraocular lens, comprising:
   a first group including an optical part (1); a soft haptic (14) including an insertion channel and a protrusion, wherein the optical part and the soft haptic are integral; and a rigid haptic (5) including a lever (8) and a thickening portion, wherein the lever is disposed within the insertion channel; and
   a second group including a rigid incomplete inner curving ring (9) including a curving flap (10), wherein the curving flap includes a clipping hole; and a soft outer ring (11) including a groove and an angled flap, wherein the incomplete inner curving ring is disposed within the groove;
   wherein the first group is connected to the second group when the thickening portion is lodged in the clipping hole and the protrusion is lodged in the angled flap; and
   wherein the outer ring and the incomplete inner curving ring are configured to allow changes in a curvature and a thickness of the lens when accommodating and to remain stable when not accommodating.

2. The accommodative intraocular lens of claim 1, wherein the soft haptic (14) includes a centering hole (4).

3. The accommodative intraocular lens of claim 1, wherein the soft haptic (14) extends radially from a perimeter of the optical part (1).

4. The accommodative intraocular lens of claim 1, wherein the soft haptic includes at least two soft haptics.

5. The accommodative intraocular lens of claim 1, wherein the soft haptic is disposed at an angle of 5° to 180° relative to a horizontal axis (19) of the lens.

6. The accommodative intraocular lens of claim 1, further comprising an equal number of the soft haptic and the rigid haptic.

7. The accommodative intraocular lens of claim 1, wherein the thickening portion (7) and the lever (8) are disposed at opposite ends of the rigid haptic.

8. The accommodative intraocular lens of claim 1, wherein the rigid haptic includes a centering hole.

9. The accommodative intraocular lens of claim 1, wherein the thickening portion (7) and the lever (8) are disposed on opposite sides of the rigid haptic.

10. The accommodative intraocular of claim 1, wherein the groove includes an opening oriented to an inside of the outer ring.

11. The accommodative intraocular lens of claim 1, wherein the angled flap (13) includes a pair of angled flaps and the protrusion includes a pair of protrusions.

12. The accommodative intraocular lens of claim 11, wherein the pair of angled flaps (13) each include a centering hole (16).

13. The accommodative intraocular lens of claim 11, wherein each of the protrusions (18) is configured to fasten to one of the pair of angled flaps.

* * * * *